United States Patent [19]

Marks

[11] Patent Number: 5,217,484
[45] Date of Patent: Jun. 8, 1993

[54] RETRACTABLE-WIRE CATHETER DEVICE AND METHOD

[76] Inventor: Michael P. Marks, 4216 Bettina Ave., San Mateo, Calif. 94403

[21] Appl. No.: 712,191

[22] Filed: Jun. 7, 1991

[51] Int. Cl.⁵ ............................................. A61M 29/00
[52] U.S. Cl. ..................................... 606/200; 128/899
[58] Field of Search ............... 606/195, 198, 200, 191; 128/899; 210/448; 623/1, 12

[56] References Cited

U.S. PATENT DOCUMENTS

| | | | |
|---|---|---|---|
| 4,169,464 | 10/1979 | Obrez . | |
| 4,425,908 | 1/1984 | Simon . | |
| 4,494,531 | 1/1985 | Gianturco . | |
| 4,619,246 | 10/1986 | Molgaaro-Nielson et al. | 128/899 |
| 4,957,501 | 9/1990 | Lahille et al. | 128/899 |
| 4,969,891 | 11/1990 | Gewertz | 128/899 |
| 4,994,069 | 2/1991 | Ritchart et al. | 606/200 |

OTHER PUBLICATIONS

Collins Jr., E. R., "Implantable Electrode for Critical Locations," NASA Tech Briefs, Aug. 1990, p. 74.

Primary Examiner—C. Fred Rosenbaum
Assistant Examiner—William W. Lewis
Attorney, Agent, or Firm—Peter J. Dehlinger; Vincent M. Powers

[57] ABSTRACT

Apparatus and method for placing a vaso-occlusion wire at a selected site in a vessel. The apparatus includes a catheter, and a pusher-and-wire assembly in which a vaso-occlusion wire is held in an axially clamped position until the wire has been advanced beyond the end of the catheter. The assembly may be adapted for guiding the catheter to the site, either by flow-directed or wire-directed movement.

29 Claims, 8 Drawing Sheets

RETRACTABLE-WIRE CATHETER DEVICE AND METHOD

FIELD OF THE INVENTION

The present invention relates to a retractable-coil catheter device, a pusher-and-coil assembly, a vaso-occlusion coil, and to a method for placing a vaso-occlusion coil at a selected site in a vessel.

BACKGROUND OF THE INVENTION

Vaso-occlusion wires are used in treating vascular conditions in which it is desired to occlude a region of a vessel or an aneurism within a vessel. The wire is introduced by first positioning a catheter at the selected site to be occluded, then advancing the wire through the catheter and into the site. The wire itself is typically a soft wire coil which can assume a linear condition for advancement though the catheter, and assume a convoluted configuration designed to "fill" the vessel or aneurism into which the coil is introduced, as described for example in U.S. Pat. No. 4,994,069.

Commonly, the vaso-occlusion wire must be placed at a remote, small-vessel site which can be accessed only through a tortuous vessel path involving multiple vessel branches, sharp turns at a vessel branch point, and/or small-diameter vessels, e.g., less than 2–5 mm. Such sites can be accessed only with a flexible, small-diameter catheter, e.g., a polyethylene-tube catheter having a distal-end inner diameter of 10–30 mils. Such a catheter is typically guided through a tortuous vessel by a guidewire having a bent tip whose direction can be controlled, to steer the catheter along a selected path.

After the catheter has been placed at the intended site, the guidewire is removed and the catheter is loaded with a vaso-occlusion wire, which is then advanced through the catheter with a pusher. When the wire is advanced beyond the end of catheter at the vaso-occlusion site, it assumes its convoluted shape designed to fill the vessel space into which it is placed.

One limitation of the above vaso-occlusion method just described is the difficulty in controlling the orientation and position of the wire in the vessel, or aneurism, after it is ejected from the catheter. For example, the wire may fail to anchor itself firmly in the vessel, and thus be carried by blood flow to a site downstream of the intended vaso-occlusion site. In addition, the wire may improperly orient itself at the site, producing incomplete vaso-occlusion. In either case, the vaso-occlusion procedure may be only partially effective.

SUMMARY OF THE INVENTION

It is a general object of the present invention to provide an improved method and catheter apparatus for placing a vaso-occlusion coil at a selected vessel site.

The invention includes, in one aspect, catheter apparatus having a catheter designed for placement at a selected vessel site, a vaso-occlusion wire which is extendable from a relaxed, convoluted condition, to an extended, linear condition in which the wire can be advanced through said lumen, and a pusher designed for advancing the wire through the catheter. Confronting ends of the pusher and wire are provided with clamping structure for holding the wire in clamped engagement with the pusher, as the wire is advanced through the catheter lumen. The clamped condition of the structure is released when a selected portion of the wire has been advanced beyond the distal catheter end, to release the wire into the vessel site.

In one embodiment, the clamping structure includes an axial enlargement carried on the wire, and expandable jaws associated with pusher, for movement between a closed condition produced by contact of the jaws with the catheter lumen, in which the jaws are effective to hold the axial enlargement in clamped engagement, and an open condition produced by expansion of the jaws, to release the axial enlargement in the wire.

The catheter apparatus may be designed for flow-directed or wire-directed catheter guidance to the site. For flow-directed guidance, the wire additionally includes a distal-end segment which is expandable, when advanced beyond the distal end of the catheter, to enhance movement of the segment in the direction of highest fluid flow. For wire-directed guidance, the wire additionally includes a distal-end segment which assumes a bent configuration when the end region is advanced beyond the distal end of the catheter. The clamping structure in this embodiment is effective to transmit torque between the pusher and the wire, for orienting the bent wire tip during catheter placement.

In another aspect, the invention includes a pusher-and-wire assembly for use with a catheter which can be placed at a selected vessel site. The assembly includes a vaso-occlusion wire extendable from a relaxed, convoluted condition, to an extended, linear condition in which the wire can be advanced through the lumen of the catheter, and a pusher which is operable from the proximal catheter end to advance the wire axially, with such in its extended condition, through the catheter by contact between confronting ends of the pusher and wire. Also included in the invention is a vaso-occlusion wire device for use with a catheter and pusher of the types described above.

In another aspect, the invention includes a method for placing a vaso-occlusion wire at a selected site in a vessel. The method includes the steps of guiding the distal end of a catheter to such site, advancing through the catheter, and a vaso-occlusion wire which is extendable from a relaxed, convoluted condition, to an extended, linear condition. During wire advancing, the wire is maintained in an axially clamped condition in which the coil can be moved axially in both directions within the catheter, until a selected portion of the wire has been advanced beyond the distal end of the catheter, at which point the wire is released from its clamped condition.

The method may be adapted for use in guiding the catheter to the selected vaso-occlusion site through a branched vessel path by flow-directed or wire-directed movement of the catheter's distal end, employing one of the modified wires described above.

These and other objects and features of the invention will become more fully apparent when the following detailed description of the invention is read in conjunction with the accompanying drawings.

DETAILED DESCRIPTION OF THE INVENTION

Catheter Apparatus

Figure 1:
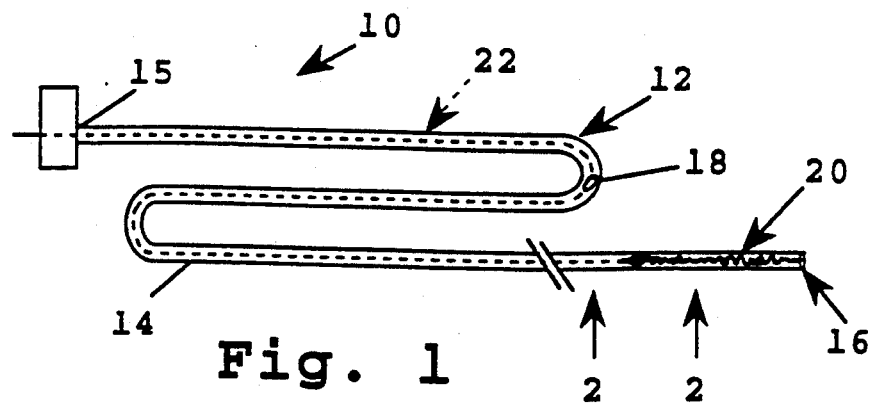
FIG. 1 shows a catheter apparatus constructed according to a general embodiment of the invention.

FIG. 1 shows a vaso-occlusion catheter device, or apparatus 10 constructed according to the present invention. The device generally includes a catheter 12 formed of an elongate tubular member 14 having proximal and distal ends 15, 16, respectively. The tubular member is preferably between about 50-300 cm in length, typically between about 100-200 cm in length. An inner lumen 18 (FIGS. 2 and 3) extends between the two ends.

The catheter is designed conventionally for accessing a vessel site at which vaso-occlusion is desired. Typically, the vessel site is within a small-diameter vessel having 2-5 mm lumen diameter, and is accessible by way of a tortuous vessel path which may involve sharp vessel turns and multiple vessel branches. For accessing such vessel sites, the catheter preferably has a small-diameter, flexible-tube construction, with a lumen diameter of less than about 40 mil, and preferably between about 12-30 mil. Catheters of this type are commercially available, for example, for accessing deep brain vascular sites.

Although not shown in FIG. 1, the catheter device may include a guidewire useable with the catheter to guide the distal catheter end toward the intended vaso-occlusion site. Guidewires of this type are commercially available, and generally include an elongate wire having a tapered, wire-wound distal end region which is adapted to be threaded through a tortuous vessel path, with the catheter being moved axially along the advanced guidewire. Once the catheter has been guided to the selected vaso-occlusion site, the guidewire can be removed from the catheter.

Figure 8A:
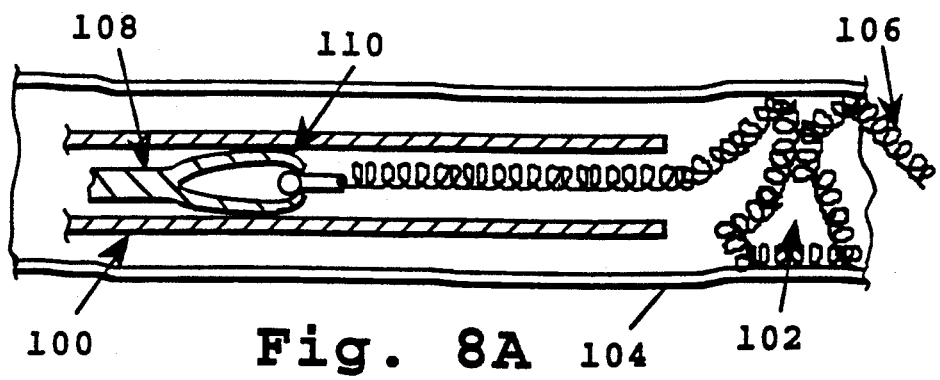
FIGS. 8A and 8B illustrate the method of wire placement in a vessel, in accordance with the method of the invention.
Figure 8B:
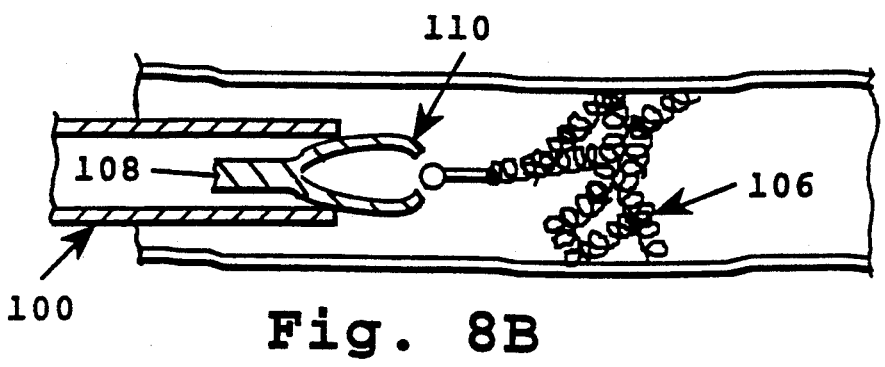

Also included in the apparatus is a vaso-occlusion wire 20 which is extendable from a relaxed, convoluted condition shown, for example, in FIGS. 8A and 8B, to an extended, linear condition, shown in FIG. 1, in which the wire can be advanced axially through the catheter lumen. The wire is moved through the catheter by a pusher 22 in the apparatus which is operable from the proximal end of the catheter. The construction of the wire and pusher are detailed below.

According to one feature of the invention, the wire and pusher are held together in clamped engagement at their confronting ends in the catheter by clamping structure or means 24 associated with the wire and pusher, as will be detailed below. The clamping engagement of the wire and pusher are designed to be released, in accordance with the invention, by catheter structure or means adjacent the catheter's distal end. The clamping and release structure are also detailed below.

Figure 2:
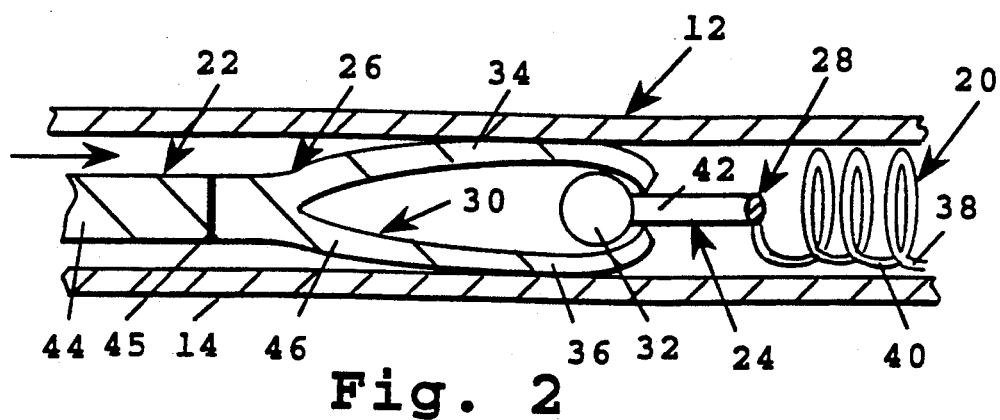
FIG. 2 is an enlarged, fragmentary view of a wire-and-pusher assembly taken generally along line 2—2 in FIG. 1.

FIG. 2 is an enlarged view of the catheter apparatus, taken generally along the region 2—2 in FIG. 1, and showing details of clamping structure 24 associated with confronting ends 26, 28, of pusher 22 and wire 20, respectively. The clamping structure in the FIG. 2 embodiment includes a jaw-like clamp 30 forming the distal end portion of the pusher, and a radial enlargement 32 forming the proximal end portion of the wire. The clamp has a pair of opposed jaws 34, 36 which are expandable between a closed condition produced by contact of the jaws with the catheter lumen, as shown in FIG. 2, and an open condition in which the jaws are in a relaxed, somewhat expanded condition, shown in FIG. 4. The radial enlargement in the wire is dimensioned for positive clamping by the jaws, with such in their closed condition (FIG. 2) and for release from the jaws, in an axial direction, with the jaws in their open condition (FIG. 4).

Figure 4:
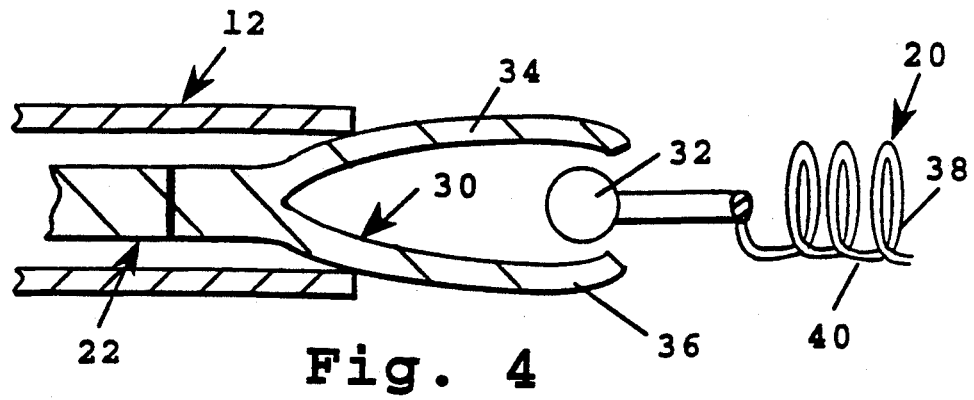
FIG. 4 illustrates one mechanism of wire release in the apparatus of the invention.

In one general embodiment, the extendable portion of wire 20 takes the form of a coil, such as indicated at 38 in FIGS. 2 and 4, formed by wrappings or windings of a fine wire thread 40, preferably 0.002 mils to 0.006 mils platinum, tungsten, or gold thread which is available, for example, from California Fine Wire Company (Grover City, Calif.). The windings are preferably made by wrapping the thread on a spinning mandrel, according to known wire-manufacturing methods. The wire advance on a mandrel is adjusted to produce a single-layer wire with a minimum helical pitch, i.e., in which the windings are close packed. Typically, the mandrel has a diameter of between 5-25 mils (1/1000 inch), yielding a wire whose outer diameter is between about 10-30 mils. The soft, flexible wire produced on the mandrel is cut to desired lengths after removal from the mandrel. For wires intended for use in vessels with diameters of about 2 mm and smaller, the wire has a preferred length of about 3-6 cm. For vessels in the 2-6 mm range, wire lengths of between about 5-10 cm are preferred.

The relaxed, convoluted shape of the coil is achieved by shaping the wire, i.e., by wrapping the wire about a larger-diameter mandrel to form a helical shape, e.g., having a helical diameter between 2-6 mm, respectively. The wire may be further deformed to contain irregularities in the helical winding, such that the wire adopts a folded, convoluted conformation in a relaxed condition, as illustrated in FIG. 8A. The irregularities are preferably made by deforming, as by twisting, the wire in the region of desired bends with the wire on the helical winding mandrel.

After shaping, the coil is treated at about 800° F. for 24 hours for memory retention after it is shaped. The memory in the coil is effective to return the wire from a stretched, linear condition in which it is advanced through a catheter to a randomly oriented, spaced-filling relaxed condition as the wire is released from the catheter. The high memory in the wire is achieved, in part, by the overall length of the thread used in forming the coil, i.e., the high ratio of thread length change in wire shape.

Alternatively, the extendable portion of the vaso-occlusion wire may be formed from a flexible, preshaped polymer tube or rod. The convoluted shape of the tube or rod may be achieved by a combination of a helical winding and/or irregularities which are imparted during heat treatment, or by shaping the wire as it is extruded, before cooling, or by injection molding. Suitable polymers for use in preparing this type of wire include any biocompatible polymer such as polyethylene, polyurethane, polypropylene, an the like, which are capable (by their inherent memory) of substantially reversible shape-retention between extended and preformed, relaxed conditions.

With continued reference to FIG. 2, the proximal end of the wire (the end confronting the pusher in the catheter) includes a stem 42 which connects the coiled portion of the wire to radial enlargement 32. The stem and radial enlargement may be formed by extrusion or molding a suitable biocompatible polymer material. The stem is attached to the coil by an adhesive or solder. Alternatively, where the extendable portion of the wire is formed of a polymer tube or rod, the stem and radial enlargement can be formed integrally with the extendable portion.

Pusher 22 shown in FIG. 2 is formed of a conventional guidewire 44 which is designed for axial movement within the catheter, by manipulation of the guidewire's proximal end at the proximal end of the catheter. The guidewire has a typical diameter of between about 8-18 mils, for use with a catheter having a lumen diameter of between about 15-30 mils, respectively. Although not shown here, the guidewire may have a more flexible distal end region formed of a reduced diameter taper in the distal region of the guidewire, and this tapered region may be reinforced, for greater column strength, by a wire wrapping, according to known guidewire construction.

The clamp in the pusher wire may be formed from a metal or polymeric rod having suitable shape-retention and resilience properties. Polymer rods suitable for use in forming the clamp include polyethylene, Teflon TM, polypropylene, and polycarbonate. The rod typically has a diameter approximately that of the guidewire, e.g., between 8-18, and a length between about 0.5-2 cm. To form the clamp, the rod is cut axially through a center plane along a major portion of the rod length. This cut forms two hemicylindrical rod sections which will form the jaws of the clamp. These jaws are formed by shaping the rod sections about a shaping member having a cross-sectional shape similar to that of the region between the jaws in FIG. 4. Shaping of the rod sections over the shaping member may be accomplished by forcing the rod sections over the shaping member, in the case of metal jaw members, or by heat-shaping the rod sections over the shaping member, in the case of a heat-shapable polymer material. The shaping is preferably carried out to form the jaws in their open positions, such as illustrated in FIG. 4, requiring a slight compressive force on the jaws to place the clamp in its closed condition. The clamp is attached to the distal end of the guidewire by a solder or adhesive attachment 45, to form the pusher.

It will be appreciated that the clamp may have three of more jaws which are movable toward and away from the axis of the clamp, between a relaxed, open condition, and a compressed clamping condition. A multi-jaw clamp of this type can be formed as above, where a suitable rod is cut axially into three of more rod sections, and the sections are shaped to form the jaws of the clamp. A multi-jaw clamp has an advantage over the two-jaw clamp shown in FIGS. 2 and 4, in that the stem carrying the radial enlargement in the wire is positively oriented in an axial direction during axial movement of the wire through an beyond the distal end of the wire.

The pusher and wire described above with reference to FIGS. 1 and 2 form, collectively, a pusher-and-wire assembly 46 which forms another aspect of the invention. The assembly is designed for use with a catheter, such as catheter 12, in placing a vaso-occlusion wire at a selected vascular site, and at a selected configuration at the site.

Figure 3:
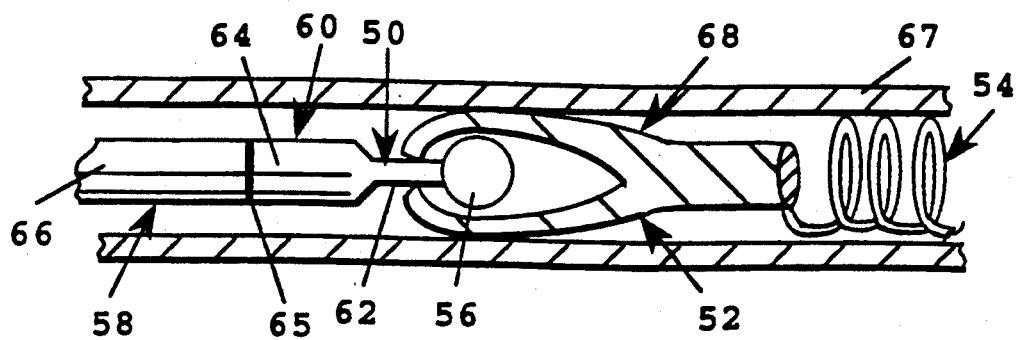
FIG. 3 is an enlarged, fragmentary view of a second embodiment of a wire-and-pusher assembly in the invention.

FIG. 3 illustrates a clamping structure 50 similar to structure 24 shown in FIG. 2, but in which a clamp 52 forms the proximal end of a vaso-occlusive wire 54, and a radial enlargement 56 captured in the clamp is formed at the distal end of a pusher 58. The clamp may be formed as described above, for attachment to one end of a coil. As shown the radial enlargement is preferably formed at the end of a rod segment 60 having a reduced-diameter stem 62 and a base 64 attached, at a solder or adhesive attachment 65, to the distal end of a guidewire 66. The clamp structure shown in FIG. 3 functions substantially identically to the structure shown in FIG. 2, as will be seen. The pusher and wire in this embodiment form a pusher-and-wire assembly 68 for use with a catheter, such as catheter 67, for placement of a vaso-occlusion wire at a selected vascular site.

FIG. 4 illustrates the distal end region of catheter 12 shown in FIGS. 1, and 2, illustrating the clamping structure in the apparatus in a release condition. In this embodiment, clamp 30 is retained in its clamped condition by contact with the inner lumen of catheter 12, and allowed to expand to its open, release condition when the pusher is moved axially to a position in which the clamp jaws are just beyond the distal catheter end. As seen and described above, jaws 34, 36 in the clamp are spread sufficiently in the open clamp condition to allow radial enlargement 32 to escape, in a axial direction, from the clamp, thus releasing the wire from the pusher.

In this embodiment, the distal end of the catheter acts as means for releasing the clamped engagement of the wire to the pusher, as the clamp has been advanced beyond the distal catheter end. The catheter distal end plays a similar role in releasing the clamped engagement of wire and pusher in the FIG. 3 embodiment, when the clamp associated with the wire is advanced beyond the distal end of the catheter.

Figure 5:
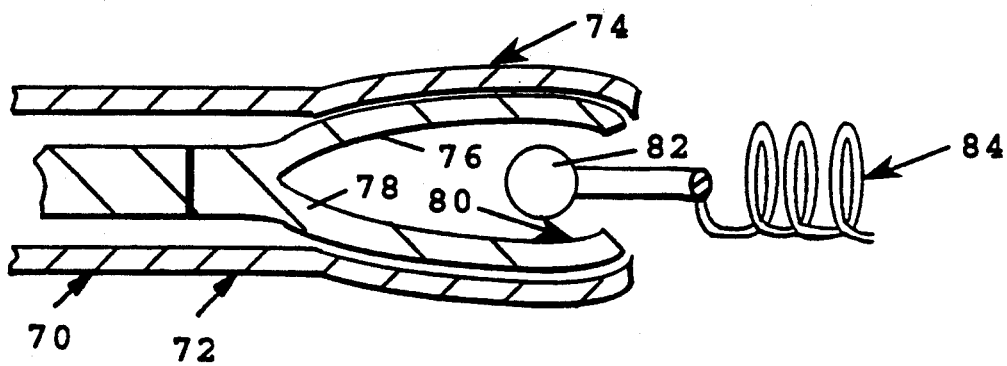
FIG. 5 illustrates a second mechanism of wire release in another embodiment of the invention.

FIG. 5 illustrates clamp release means in a catheter apparatus 70 like that described above, but having a catheter 72 whose distal end region contains a radially enlarged segment 74. The greater lumen wall diameter in segment 74 is designed allow expansion of jaws 76, 78 in a pusher clamp 80, as indicated, to allow axial release of a radial enlargement 82 forming one end of a wire 84, for wire release. The pusher and wire are constructed as described above with respect to FIG. 2. In this embodiment, the enlarged catheter segment serves as the release means in the apparatus for releasing the clamped engagement of the pusher to the wire. It is noted that the clamping structure shown in FIG. 3 would not be suitable for use in the FIG. 5 present release means, since the wire in the FIG. 3 embodiment would be released from the pusher, but not from the catheter by positioning the clamp in the enlarged catheter segment.

Figure 6:
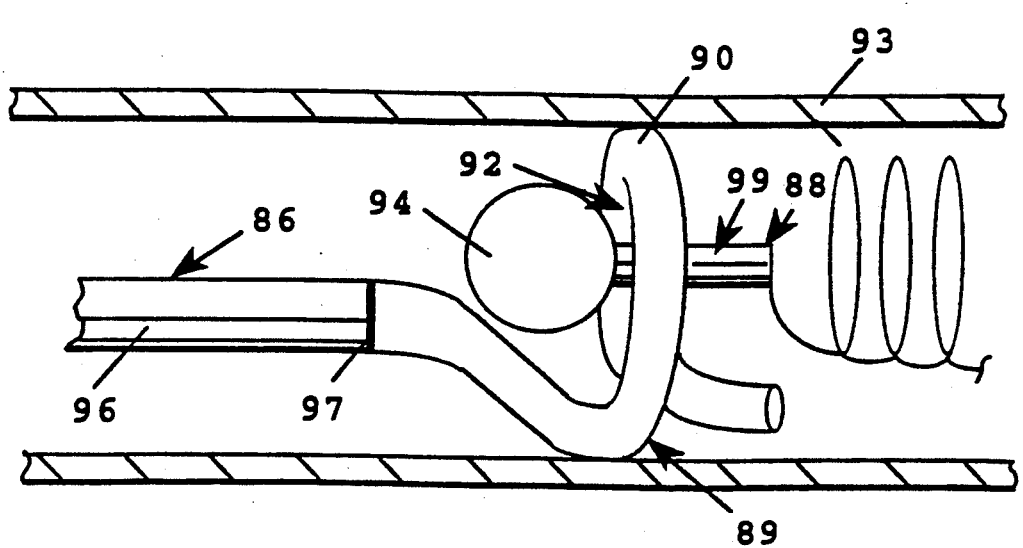
FIG. 6 illustrates another embodiment of a pusher-and-wire assembly in the invention.
Figure 7:
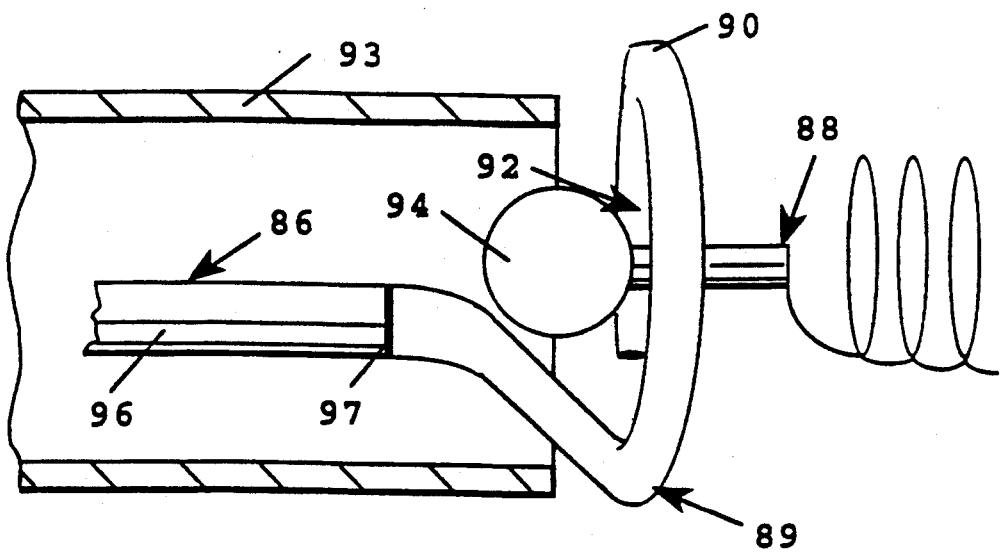
FIG. 7 illustrates the mechanism of wire release in the FIG. 6 assembly.

FIGS. 6 and 7 illustrate a second general type of clamp structure for clamping a vaso-occlusive wire axially to the confronting end of a pusher in a catheter. The figures show the distal end region of a pusher 86 and the confronting, proximal end of a vaso-occlusive wire 88 which is clamped to the pusher. The pusher in this embodiment has a coiled-loop clamp 89 formed by a helically looped segment 90. The loop is constructed to assume, in a relaxed condition, the expanded loop configuration shown in FIG. 7 in which the center region 92 of the segment loop is large enough to allow axial escape of a radial enlargement 94 forming the confronting end of wire 88. When the loop is disposed within a catheter, such as the one indicated at 93, its more tightly coiled configuration serves to capture the wire's axial enlargement as shown in FIG. 6.

Wire 88 in the just-described clamping structure may have substantially the same construction as described for wire 20 in apparatus 10. Pusher 86 is formed by joining segment 90 to a standard guidewire 96, at a solder adhesive attachment 97. The segment may be formed from a polymer rod whose coiled region is reduced in diameter and shaped by heating, or which is formed by extrusion with a reduced-diameter end region and shaped in the desired helical loop under heated conditions. The pusher and wire form a pusher-and-wire assembly 99.

Although not shown here, the clamping structure shown in FIGS. 6 and 7 can be modified so that the coiled-loop clamp is carried on the vaso-occlusive wire, and the radial enlargement is carried on the pusher, analogous to the configuration shown in FIG. 3. In this embodiment, the wire may be formed from a polymer rod or tube, with the extendable portion of the wire having the desired convolutions in the relaxed state, and a proximal end segment of the wire having a coiled loop which is expandable between a reduced-diameter, clamping condition, within the catheter, and a relaxed, release condition outside the lumen of the catheter.

In either configuration, the distal end 95 of catheter 93 provides means for releasing the clamped engagement of the of the wire to the pusher, as the clamp is advanced beyond the distal catheter end.

Wire-Placement Method

The operation of the apparatus, for use in placing a vaso-occlusion wire at a selected site in the vascular system, will be described with reference to FIGS. 8 and 9. In a typical operation, the vaso-occlusion site is accessible by a tortuous, small-vessel path which may include multiple vessel turns or bends, and one or more vessel branches. The catheter is guided to such a site, conventionally, by the use of a catheter and guidewire, where the guidewire is used for steering along the path, and the catheter is periodically advanced along the guidewire. The vaso-occlusion site may be an aneurism which is to be blocked, or a region in a small vessel which it is desired to occlude.

After the catheter has been guided to the selected site, and the guidewire removed, the extended vaso-occlusion wire and pusher are inserted into the proximal end of the catheter, with the wire clamped to the pusher's clamping structure. In the embodiment shown in FIG. 2, the extended wire is first inserted into the catheter with only the radial enlargement at the wire's proximal end showing. The pusher clamp is placed over the enlargement and the clamp and enlargement are then pushed into the catheter, compressing the clamp jaws to their clamping condition. The pusher is now advanced axially along the catheter, pushing the extending vaso-occlusion wire toward the selected vascular site.

FIGS. 8A and 8B show the distal end of a catheter 100 placed adjacent a selected occlusion site 102 within a small-diameter vessel 104. FIG. 8A shows the configuration of a wire 106 as it is advanced out of the catheter into the vessel, illustrating the convoluted, relaxed state which the wire assumes as it is released from the catheter. When the extended portion of the wire has been released, but before the wire is unclamped from the pusher, the user can view the position and configuration of the wire in the vessel, e.g., by fluoroscopy or angiography. If wire placement is not correct, or the wire has not assumed a desired space filling configuration, the user can adjust the wire position by movement of the catheter in one direction or another.

When the desired position and orientation of the wire have been achieved, the user now advances a pusher 108 slightly to a clamp-release position, to release the wire from the catheter and pusher clamp 110, as illustrated in FIG. 8B. The catheter and pusher can now be retracted from the site, leaving the vaso-occlusion wire in place.

Figure 9A:
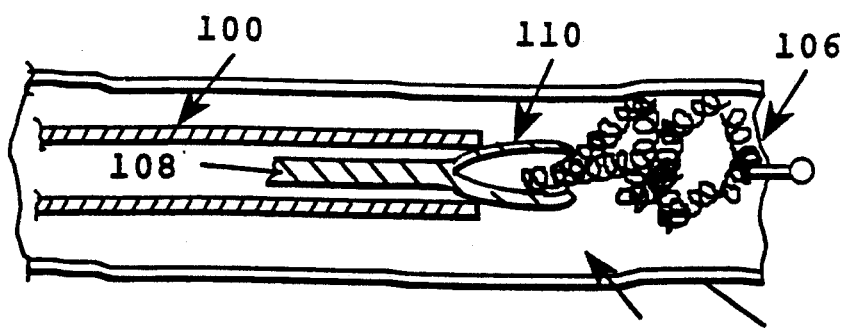
FIGS. 9A-9D illustrate steps in a method of wire retrieval or repositioning, in accordance with a further aspect of the method of the invention.
Figure 9B:
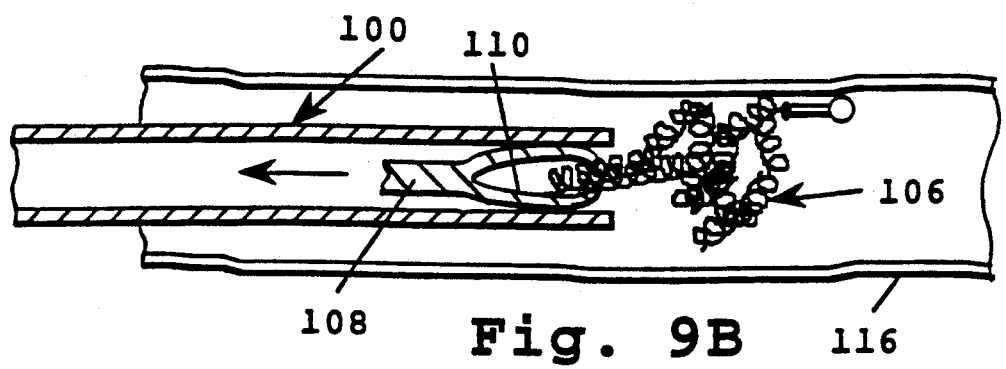

FIGS. 9A-9D illustrate how the apparatus illustrated in FIGS. 8A and 8B can be used to adjust the position or orientation of vaso-occlusion wire 106, after deposition of wire at a vaso-occlusion site 114 in a vessel 116, or to retrieve a wire from a vessel site. In FIG. 9A, the wire is shown in a relaxed convoluted configuration, but where the lower portion of the vessel is substantially unblocked by the wire, with the wire wedged between opposite side walls of the vessel. As a first step in the operation, the catheter and pusher, with the jaws in an open condition, are advanced to place the jaws over a section of the wire, as indicated in FIG. 9B.

Figure 9C:
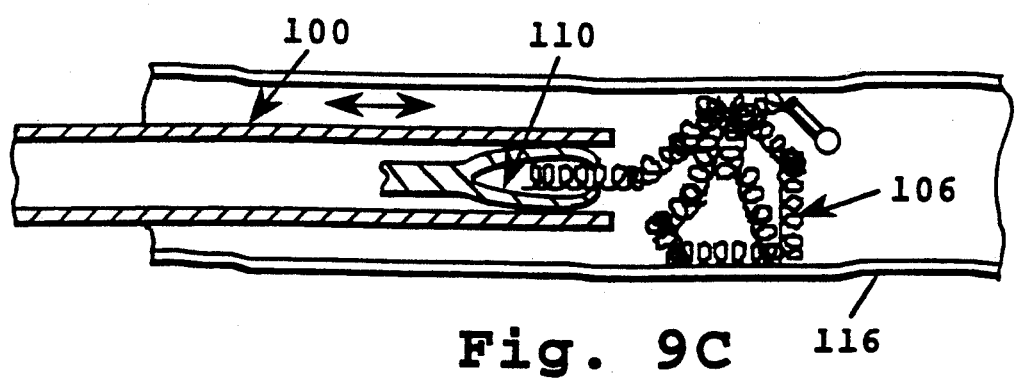
Figure 9D:
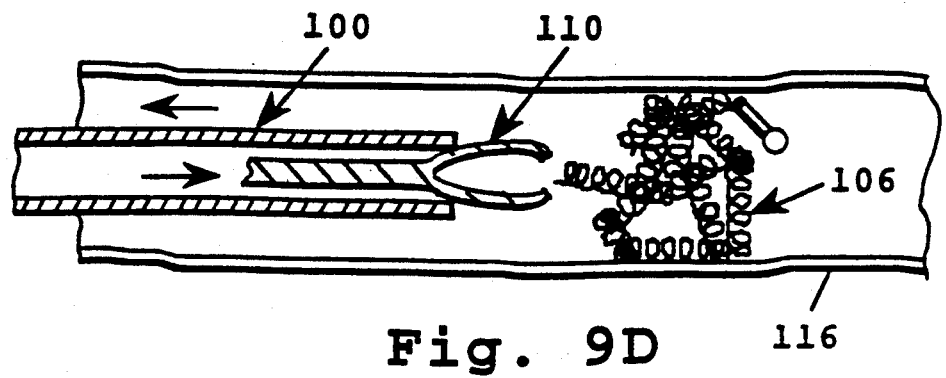

In the second step, the pusher is retracted into the catheter, to close the jaws of the clamp, and thereby clamp a portion of the wire to the pusher. The catheter and pusher can now be moved as a unit, either to adjust the position and orientation of the wire, as shown in FIG. 9C, or to retract the wire from the site. Finally, when a selected coil position and orientation are achieved, the pusher is advanced to an open-clamp position, releasing the wire from the catheter, illustrated in FIG. 9D.

Although the operation of the apparatus, in a wire-placement procedure, has been described with respect to the apparatus described with respect to FIGS. 1, 2, and 4, it will be appreciated how the procedure can be carried out in a similar fashion by alternative embodiments of the apparatus, such as those illustrated in FIGS. 3, and 5-7.

Catheter Guidance Wire and Method

In the procedure outlined in Section B, the catheter was first placed at a selected vaso-occlusion site by use of a guidewire to guide the catheter through a tortuous vessel path to the site. In the embodiments of the invention described in this section, the vaso-occlusion wire is itself adapted for use in guiding the catheter to the selected site. As will be seen, this approach is made possible by the ability to advance the extended vaso-occlusion wire both distally and proximally within the catheter, by means of the clamping structure in the apparatus, described above. The advantage of the approach is that the steps of first positioning the catheter with a guidewire, then removing the guidewire, and replacing the guidewire with a pusher-and-wire assembly are combined into a single step.

Figure 10A:
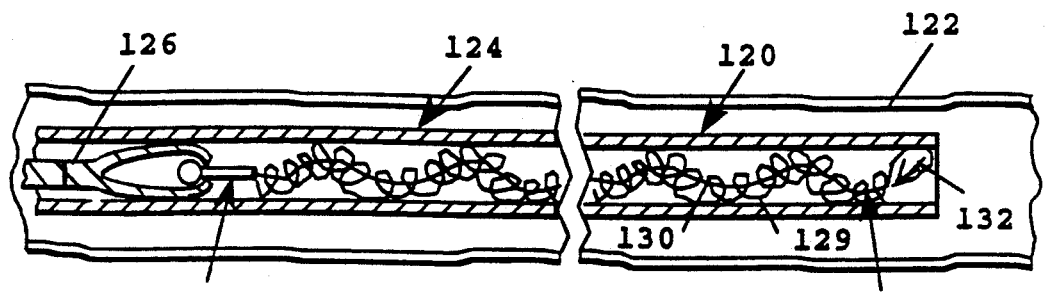
FIGS. 10A and 10B illustrate a vaso-occlusive wire constructed, according to another embodiment of the invention, for use in flow-directed catheter placement, at retracted (10A) and extended (10B) positions in a catheter.
Figure 10B:
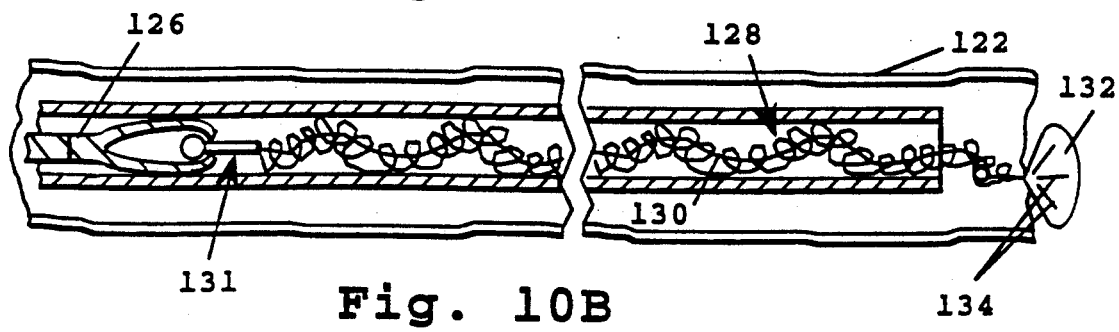
Figure 11:
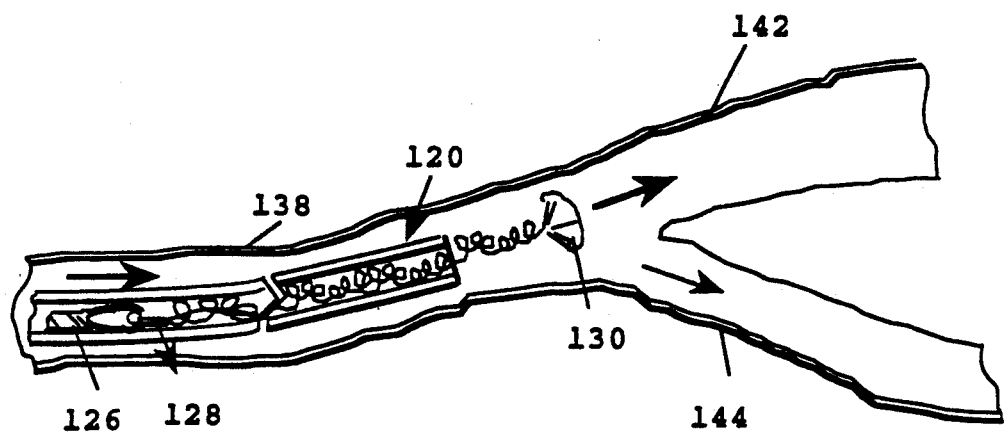
FIG. 11 illustrates the method of flow-directed guidance employing the FIG. 10 wire.

The embodiment of the invention illustrated in FIGS. 10 and 11 is intended for catheter guidance by flow-directed movement of a catheter in the direction of highest fluid flow. FIGS. 10A and 10B show a distal end region of a catheter apparatus 120 designed for such flow directed movement through and within a vessel 122. The apparatus includes a catheter 124, a pusher 126, and a vaso-occlusion wire 128. The pusher and wire are secured in a clamped condition in the wire by clamping structure 128 such as described above with respect to FIG. 2. Apparatus 120 differs from that shown in FIGS. 1 and 2 only in the construction of wire 128, as follows.

Wire 128 is formed of a coil winding 129, like wire 20, but includes a central thread 130 which connects opposed ends of the wire. The purpose of thread 130 is to allow the wire to be retracted within the catheter by pulling the pusher proximally within the catheter. Without thread 130, such pusher movement would be accommodated primarily by the stretching in the wire coil, rather than retraction of the entire wire as a unit. The wire may be formed as above, but with the inclusion of a central thread during the coil-winding process. After the coil is formed and cut, the central thread is attached, as by soldering to the opposite coil ends, and the coil is given its convoluted, relaxed shape, as above.

Wire 120 is also modified to include a sail or parachute 130 attached to the distal end of the coil. The parachute is formed of an expanse 132 of flexible material, such as thin polyethylene film, which is tied to the coil end by tie lines, such as lines 134. As shown in FIG. 10B, the parachute can be fully withdrawn into the catheter, by pulling the clamped wire proximally with the pusher. When the pusher is advanced distally, as in FIG. 10B, the parachute is advanced beyond the distal end of the catheter, and can "open" in blood flow past the parachute (indicated by arrows 136 in the figure). That is, the parachute, which is also referred to herein as flexible distal-end structure, is open to provide increased area of contact with blood flowing through the vessel in a left-to-right direction in the FIG. 144

In this condition, the distal end of the catheter is carried in the direction of greatest blood flow.

The operation of apparatus 120 in a catheter guidance method is illustrated in FIG. 11, which shows the distal end of the catheter in a vessel 138, just upstream of a vessel branch 140 at which the vessel bifurcates into larger and smaller vessels 142, respectively. It is assumed that the desired direction of movement of the catheter is into vessel 142 having the greater volume-flow rate. When the vessel branch is reached, the user advances the pusher to move the distal end of wire 128 from its position shown in FIG. 10A to that shown in FIG. 10B where the parachute is open and carried in the direction of greater blood flow, i.e., toward vessel 142, as indicated.

The catheter is now advanced as a unit, with blood flow tending to carry the catheter end into vessel 142. After the catheter end is within vessel 142, the pusher may be retracted to draw the parachute into the distal catheter end. The parachute is maintained in its withdrawn position (FIG. 10A) when a vessel branch is encountered, and it is desired to follow the smaller of the two vessel branches. Thus, catheter guidance along a series of vessel branches may be accomplished by alternately extending the parachute, when the larger of two vessel branches is to be followed, and retracting the parachute when the smaller of two branches is to be followed.

When the desired vaso-occlusion site is reached, the wire is advanced into the vessel site, and positioned and oriented as above, before being released from its clamped position.

Figure 12A:
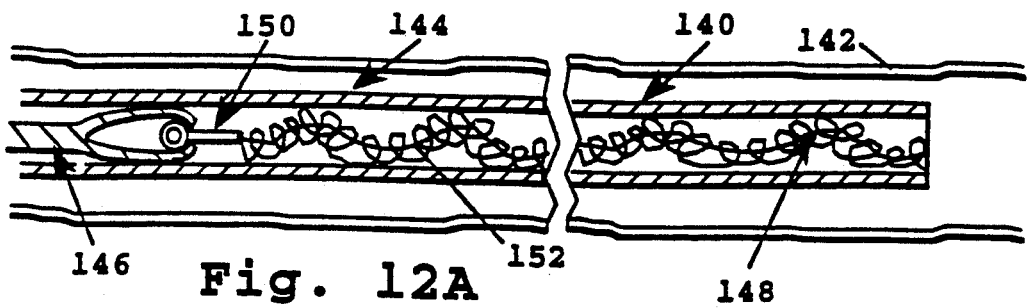
FIGS. 12A and 12B illustrate a vaso-occlusive wire constructed, according to another embodiment of the invention, for use in wire-directed catheter placement, at retracted (12A) and extended (12B) positions in a catheter.
Figure 12B:
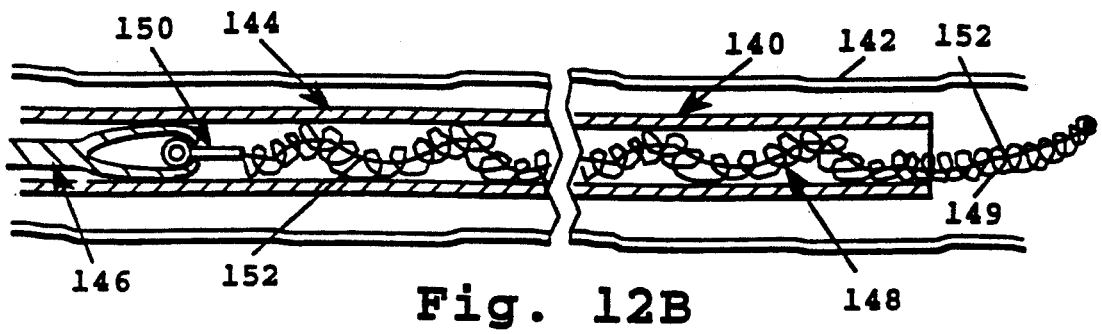
Figure 13:
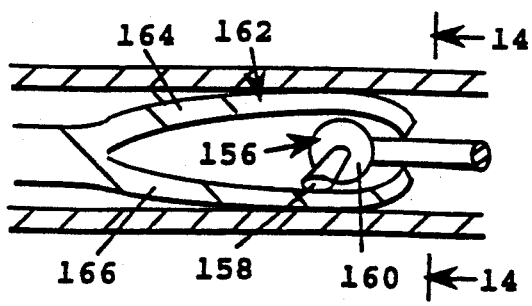
FIG. 13 shows modified clamping structures for use in the wire construction shown in FIG. 12.
Figure 14:
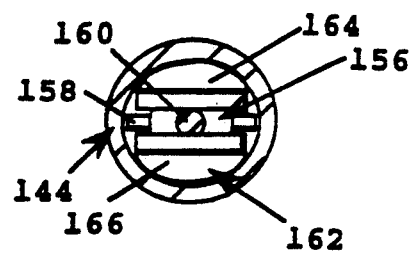
FIG. 14 is a cross-sectional view taken along line 14—14 in FIG. 13.

The embodiment of the invention illustrated in FIGS. 12-14 is intended for catheter guidance by wire-directed movement of a catheter in the direction of wire bend. FIGS. 12A and 12B show a distal end region of a catheter apparatus 140 designed for such wire-directed movement through and within a vessel 142. The apparatus includes a catheter 144, a pusher 146, and a vaso-occlusion wire 148. The pusher and wire are secured in a clamped condition in the wire by clamping structure 150 such as described above with respect to FIG. 2. Catheter 144 differs from that shown in FIGS. 1 and 2 only in the construction of wire 148, as follows.

Wire 148 is formed of a coil winding 149, like wire 20, but includes a central torqueable wire band 152 which connects opposed ends of the wire. Band 152 serves three purposes: First, it provides a substantially inelastic connection between opposite ends of the coil winding, to allow the wire to be retracted in the catheter. Secondly, it provides torqueable structure which allows wire 148 to be torqued during catheter guidance. Finally, the band provides a bent tip 154, as seen in FIG. 12B, which can be oriented for catheter guidance, as described below.

The wire also includes a modified radial enlargement 156 designed to allow transmission of torque from the guidewire to the wire. With reference to FIGS. 13 and 14, the enlargement includes a pair of radial posts, such as 158, extending from opposite sides of a spherical structure 160 which is captured in pusher clamp 162 within the catheter. As can be appreciated from FIG. 14, the posts serve to engage the sides of the clamp jaws 164, 166, when the clamp is rotated, to rotate the radial enlargement, and with it, the vaso-occlusion wire. Thus, torque applied to the pusher is effectively transmitted to the wire band, to rotate the vaso-occlusion wire within the catheter.

Figure 15A:
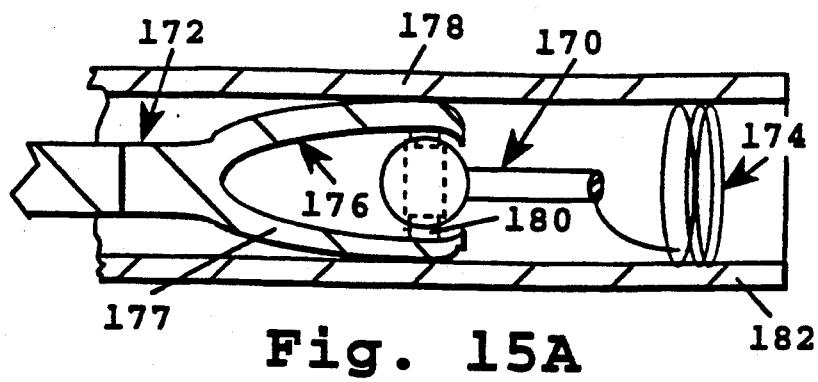
FIGS. 15A and 15B show side and sectional views of one alternative clamping structure capable of transmitting torque from a pusher to a wire.
Figure 15B:
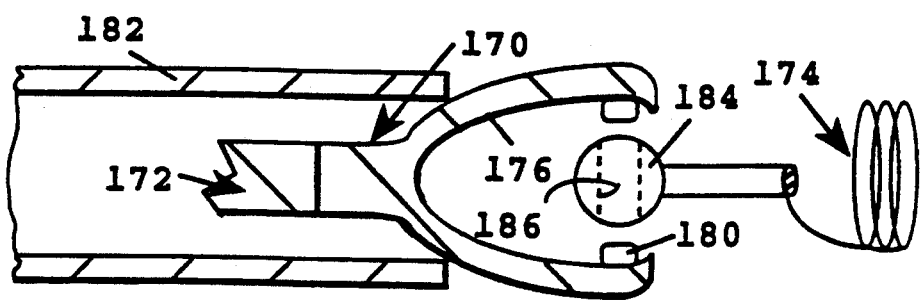

FIGS. 15 and 16 illustrate two alternative embodiments of wire-clamping structure which provide positive torque transmission between a pusher and wire in the invention, i.e., clamping structure which could be used in apparatus 140. Shown in FIGS. 15A and 15B is a clamping structure 170 which includes confronting end regions of a pusher 172 and a vaso-occlusion wire 174. A clamp 176 in pusher 172 has a pair of expandable jaws 176, 178, similar to clamp 30 shown in FIG. 2, but where each jaw includes an inwardly projecting pin, such as pin 180. The jaws are expandable between a closed position in which the jaws are constrained by contact with the lumen walls of a catheter 182, as shown in FIG. 15A, and an open condition in which the jaws are positioned beyond the distal end of the catheter, shown shown in FIG. 15B.

A radial enlargement 184 in wire 174 has a spherical shape, as in the FIG. 2 embodiment, but includes a central bore 86 dimensioned for receiving the clamp pins in the opposite ends of the bore, as shown in FIG. 15A. The locking action of the pins in the bore, in the clamp's closed condition, provides positive torque transmission between the pusher and wire, as can be appreciated.

When the pusher is advanced to move the clamp beyond the distal end of the catheter, as shown in FIG. 15B, the clamps open to their relaxed condition, freeing the radial enlargement for movement out of the jaws, as indicated.

Figure 16A:
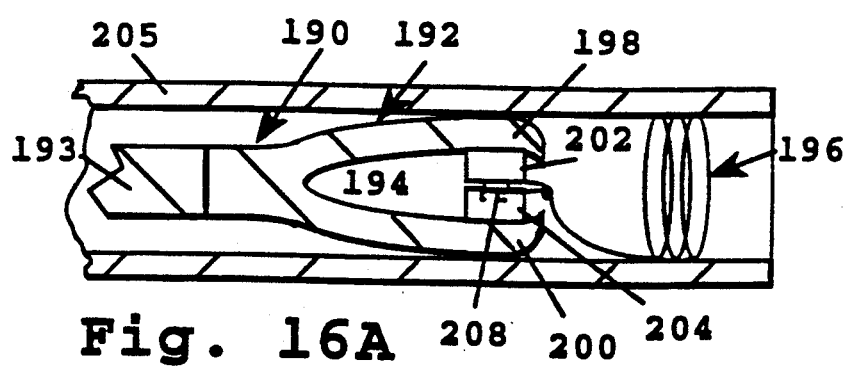
FIGS. 16A and 16B show side and sectional views of another alternative clamping structure capable of transmitting torque from a pusher to a wire.
Figure 16B:
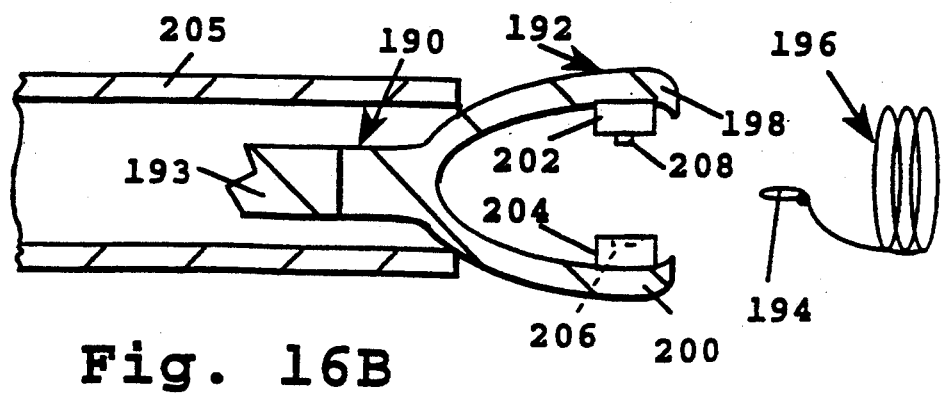

The clamping structure shown in FIGS. 16A and 16B, and indicated generally at 190, includes a clamp 192 forming the distal end of a pusher 193; and a planar loop 194 forming the proximal end of a vaso-occlusion wire 196. Clamp 192 has a pair of expandable jaws 198, 200, similar to clamp 30 shown in FIG. 2, but where each jaw includes inwardly projecting pads 202, 204, respectively which have flat confronting surfaces for contacting the wire loop, when the clamp is in a closed condition. As above, the jaws are expandable between a closed position in which the jaws are constrained by contact with the lumen walls of a catheter 205, as shown in FIG. 15A, and an open condition in which the jaws are positioned beyond the distal end of the catheter, shown in FIG. 15B.

A channel 206 formed in pad 204 is adapted for receiving a pin 208 in pad 202 when the clamp is in a closed condition. The pin prevents the wire loop from escaping from the clamp, with such in a closed condition, but readily allow the loop to be released from the clamp when the clamp opens, as shown in FIG. 16B.

Figure 17:
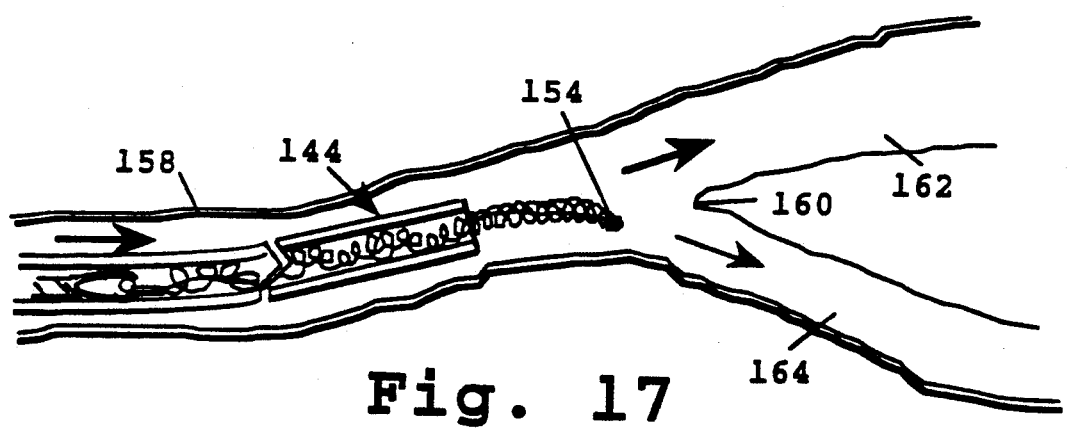
FIG. 17 illustrates the method of wire-directed guidance employing the FIG. 12 wire.

The operation of apparatus 140 in a catheter guidance method is illustrated in FIG. 17, which shows the distal end of the catheter in a vessel 158, just upstream of a vessel branch 160 at which the vessel bifurcates into larger and smaller vessels 162, 164, respectively. It is assumed that the desired direction of movement of the catheter is into vessel 164 having the lower volume-flow rate. When the vessel branch is reached, the user advances the pusher to extend wire tip 154 beyond the distal end of the catheter, as shown in FIG. 12B. The pusher is then torqued to rotate the tip in the direction of the vessel pathway, e.g., toward vessel 164, as shown in FIG. 17. The catheter is then advanced along the vessel pathway, with the wire tip guiding the catheter into the selected vessel branch. Catheter guidance along a series of vessel branches is thus achieved by employing the vaso-occlusion wire as a bent-tip guide wire, for guiding the catheter along a tortuous path to a selected vaso-occlusion site. When the site is reached, the wire is the advanced into the vessel site, and positioned and oriented as above, before being released from its clamped position.

From the foregoing, it will be appreciated how various objects and features of the invention are met. First, in the catheter operation of placing a vaso-occlusion wire at a vascular site, the present invention allows the wire to be moved within the site, under positive clamping to a pusher, until the wire is properly positioned and oriented within the site, to optimize its intended vaso-occlusion function. Secondly, even after the wire is released from the pusher, the wire can be reclamped for further orienting changes in the vessel or to retrieve the wire from the site.

The construction of the apparatus requires relatively simple modifications of confronting ends of a conventional pusher and wire, for use with a conventional catheter.

Finally, the wire in the apparatus can be readily adapted, as described in Section C, for use both in guiding a small-diameter catheter through a tortuous vessel path, and as a vaso-occlusive wire, once the selected occlusion site is reached. The wire may be designed either for flow-directed or wire-directed movement along the vessel pathway.

Although the invention has been described with respect to particular embodiments and methods, it will be appreciated that various changes and modifications may be made without departing from the invention.

It is claimed:

1. Apparatus for use in producing vaso-occlusion at a selected site in a body vessel comprising
    a catheter having proximal and distal ends and an interior lumen extending therebetween, and adapted for placement of its distal end adjacent such selected site,
    a vaso-occlusion wire extendable from a relaxed condition capable of assuming a convoluted condition, to an extended, linear condition in which the wire can be advanced through said lumen,
    a pusher which is controllable from the proximal catheter end to advance said wire, with such in its extended condition, through said catheter by contact between confronting ends of the pusher and wire,
    a radial enlargement carried on one of such confronting ends, and expandable clamping structure associated with the other of such confronting ends for movement between a closed condition produced by contact of the structure with the catheter lumen, in which the clamping structure is effective to hold the radial enlargement in clamping structure is expanded to release the radial enlargement, and
    release means in said catheter, adjacent its distal end, for releasing the clamping structure from its closed to its open condition when a selected portion of the wire has been advanced beyond the distal catheter end.

2. The apparatus of claim 1, wherein said radial enlargement is carried on said wire, and said clamping structure is associated with said pusher.

3. The apparatus of claim 1, wherein said clamping structure is an expandable coil for expansion between a closed, more coiled condition produced by contact of the coil with the catheter lumen, in which the coil is effective to hold the radial enlargement in clamped engagement, and an open, less coiled condition produced by interaction of the jaws with said release means, in which said coil is expanded to release the axial enlargement.

4. The apparatus of claim 3, wherein said radial enlargement is carried on said wire, and said coil is associated with said pusher.

5. The apparatus of claim 3, wherein said radial enlargement is carried on said pusher, and said coil is associated with said wire.

6. The apparatus of claim 1, wherein said release means is defined by the distal-end of said catheter.

7. The apparatus of claim 1, wherein said release means includes a radially enlarged segment in said catheter lumen, adjacent the catheter's distal end.

8. The apparatus of claim 1, wherein said wire includes an elongate coil whose opposite ends are connected by a substantially inelastic thread.

9. The apparatus of claim 1, for use in guiding the catheter through a branched vessel path by flow-directed movement of the catheter's distal end, wherein said wire includes flexible distal-end structure which, when advanced beyond the distal end of the catheter, is adapted to open to provide increased area of contact with blood flowing in a vessel.

10. The apparatus of claim 9, wherein said wire includes an elongate coil whose opposite ends are connected by a substantially inelastic thread.

11. The apparatus of claim 1, for use in guiding the catheter through a branched vessel path by wire-directed movement of the catheter's distal end, wherein said wire is torqueable and includes a distal end region which assumes a bent configuration when the end region is advanced beyond the distal end of the catheter, and said clamping structure is effective to transmit torque between said pusher and said wire, with such in the catheter lumen.

12. The apparatus of claim 11, wherein said wire includes an elongate coil whose opposite ends are connected by a torqueable, substantially inelastic band.

13. A pusher-and-wire assembly for use with a catheter having proximal and distal ends and an interior lumen extending therebetween and which is adapted for placement at a selected vessel site, comprising a vaso-occlusion wire extendable from a relaxed condition capable of assuming a convoluted shape, to an extended, linear condition in which the wire can be advanced through the lumen of such catheter, a pusher which is operable from the proximal catheter end to advance said wire axially, with such in its extended condition, through said catheter by contact between confronting ends of the wire and pusher, a radial enlargement carried on one of such confronting ends, and expandable clamping structure associated with the other of such confronting ends adapted for movement between a closed condition produced by contact of the clamping structure with the catheter lumen, in which the structure is effective to hold the radial enlargement in clamped engagement, and an open condition produced by expansion of the structure, in which the enlargement is axially releasable from the structure.

14. The assembly of claim 13, wherein said clamping structure includes expandable jaws adapted for movement between a relaxed, open condition and a adapted for movement between a relaxed, open condition and a closed condition produced by contact of the jaws with the catheter lumen.

15. The assembly of claim 14, wherein said radial enlargement is carried on said wire, and said jaws are associated with said pusher.

16. The assembly of claim 14, wherein said clamping structure includes an expandable coil adapted for expansion between a closed, more coiled condition produced by contact of the coil with the catheter lumen, and an open, less coiled condition, in which said coil is expanded to release the radial enlargement.

17. The assembly of claim 16, wherein said radial enlargement is carried on said wire, and said coil is associated with said pusher.

18. The assembly of claim 16, wherein said radial enlargement is carried on said pusher, and said coil is associated with said wire.

19. The assembly of claim 13, wherein said wire includes an elongate coil whose opposite ends are connected by a substantially inelastic thread.

20. The assembly of claim 13, for use in guiding a catheter through a branched vessel path by flow-directed movement of the catheter's distal end, wherein said wire includes flexible distal-end structure which, when advanced beyond the distal end of the catheter, is adapted to open to provide increased area of contact with blood flowing in a vessel.

21. The assembly of claim 20, wherein said wire includes an elongate coil whose opposite ends are connected by a substantially inelastic thread.

22. The assembly of claim 13 for use in guiding the catheter through a branched vessel path by wire-directed movement of the catheter's distal end, wherein said wire is torqueable and includes a distal end region which assumes a bent configuration when the end region is advanced beyond the distal end of the catheter, and said clamping structure is effective to transmit torque between said pusher and said wire, with such in the catheter lumen.

23. The assembly of claim 22, wherein said wire includes an elongate coil whose opposite ends are connected by a torqueable, substantially inelastic band.

24. A vaso-occlusion wire for use with a catheter having proximal and distal ends and an interior lumen extending therebetween and which is adapted for placement at a selected vessel site, and a pusher which is operable from the proximal catheter end for radial movement through the catheter lumen to a release position, said pusher including a clamping structure, comprising an extendable, torqueable wire portion which is extendable from a relaxed, convoluted condition, to an extended, linear condition in which the wire can be advanced through the lumen of such catheter, and a radial enlargement carried at one end of the wire portion for torqueable clamping engagement with and release from the clamping structure in the pusher.

25. A method for placing a vaso-occlusion wire at a selected site in a vessel, where the catheter is guided through a branched vessel path by flow-directed movement of the catheter's distal end, comprising guiding the distal end of a catheter to such site, by advancing within the catheter a vaso-occlusion wire which is extendable from a relaxed, convoluted condition, to an extended, linear condition, where said wire includes a flexible distal-end structure which, when advanced beyond the distal end of the catheter, is adapted to open to provide increased area of contact with blood flowing in a vessel, and said advancing includes (a) advancing the wire distally, to advance said segment beyond the distal end of the catheter, when it is desired to guide the catheter into a vessel branch having greater fluid flow at a branch point, and (b) retracting the wire proximally, to draw said segment within the distal end of the catheter, when it desired to guide the catheter away form a vessel branch having greater fluid flow at a branch point, and during said advancing, maintaining the wire in an axially clamped condition in which the wire can be moved axially in both directions within the catheter, until a selected portion of the wire has been advanced beyond the distal end of the catheter, at which point the wire is released from its clamped condition.

26. A vaso-occlusion wire for use with a catheter having proximal and distal ends and an interior lumen extending therebetween and which is adapted for placement at a selected vessel site, and a pusher which is operable from the proximal catheter end for radial movement through the catheter lumen to a release position, said pusher including a clamp structure, comprising an extendable, wire portion which is extendable rom a relaxed, convoluted condition, to an extended, linear condition in which the wire can be advanced through the lumen of such catheter, said extendable portion including an elongate segment whose opposite ends are connected by a substantially inelastic member, and a radial enlargement carried at one end of the wire portion for clamping engagement with and release form the clamping structure in the pusher.

27. The wire of claim 26, wherein said member is a torqueable band adapted to transmit torque from said radial enlargement along the length of the extendable portion.

28. A vaso-occlusion wire for use with a catheter having proximal and distal ends and an interior lumen extending therebetween and which is adapted for placement at a selected vessel site, and a pusher which is operable from the proximal catheter end for radial movement through the catheter lumen to a release position, said pusher including a clamp structure, comprising an extendable, wire portion which is extendable from a relaxed, convoluted condition, to an extended, linear condition in which the wire can be advanced through the lumen of such catheter, said wire including flexible, distal-end structure which, when advanced beyond the distal end of the catheter, is adapted to open to provide increased area of contact with blood flowing through a vessel, and a radial enlargement carried at one end of the wire portion for clamping engagement with and release form the clamping structure in the pusher.

29. A method for placing a vaso-occlusion wire at a selected site in a vessel, where the catheter is to be guided through a branched vessel path by wire-directed movement of the catheter's distal end, comprising guiding the distal end of a catheter to such site, by advancing within the catheter a vaso-occlusion wire which is extendable from a relaxed, convoluted condition, to an extended, linear condition, where said wire includes a distal-end segment which assumes a bent configuration when the end region is advanced beyond the distal end of the catheter, and said wire can be torqued remotely as it is advanced within the catheter, and said advancing includes (a) advancing the wire distally, to advance said segment beyond distal end of the catheter, when it is desired to guide the catheter into one of two vessels at a branch point, (b) torquing the wire to orient the bent segment of the wire in the direction of the one vessel at the branch point, and (c) advancing the wire distally to guide the catheter into the one vessel, and during the said advancing, maintaining the wire in an axially clamped condition in which the wire can be moved axial in both directions within the catheter, until a selected portion of the wire has been advanced beyond the distal end of the catheter, at which point the wire is released from its clamped condition.

* * * * *